(12) United States Patent
Stopek

(10) Patent No.: US 8,425,972 B2
(45) Date of Patent: Apr. 23, 2013

(54) ANTIMICROBIAL MATERIALS AND COATINGS

(75) Inventor: Joshua B. Stopek, Yalesville, CT (US)

(73) Assignee: Covidien LP, Mansfield, MA (US)

( * ) Notice: Subject to any disclaimer, the term of this patent is extended or adjusted under 35 U.S.C. 154(b) by 870 days.

(21) Appl. No.: 12/594,616

(22) PCT Filed: May 9, 2008

(86) PCT No.: PCT/US2008/063147
§ 371 (c)(1),
(2), (4) Date: Oct. 5, 2009

(87) PCT Pub. No.: WO2008/144247
PCT Pub. Date: Nov. 27, 2008

(65) Prior Publication Data
US 2010/0119695 A1    May 13, 2010

Related U.S. Application Data

(60) Provisional application No. 60/930,087, filed on May 14, 2007.

(51) Int. Cl.
*G06F 15/16* (2006.01)
*H04M 3/42* (2006.01)

(52) U.S. Cl.
USPC ............. 427/2.25; 549/295; 514/311; 216/58

(58) Field of Classification Search ............ 549/295; 514/311; 216/58; 427/2.25, 2.24, 2.1
See application file for complete search history.

(56) References Cited

U.S. PATENT DOCUMENTS

| | | | |
|---|---|---|---|
| 4,954,593 A | 9/1990 | Vara et al. | |
| 5,968,951 A * | 10/1999 | Dodey et al. | 514/311 |
| 7,955,512 B2 * | 6/2011 | Park et al. | 216/58 |
| 2006/0193884 A1 | 8/2006 | Stopek et al. | |
| 2007/0032666 A1 * | 2/2007 | Read et al. | 549/295 |

FOREIGN PATENT DOCUMENTS

| WO | WO 99/54323 A1 | 10/1999 |
|---|---|---|
| WO | WO 01/76594 A1 | 10/2001 |
| WO | WO 02/00639 A1 | 1/2002 |
| WO | WO 03/084322 A2 | 10/2003 |
| WO | WO 2005/053684 A1 | 6/2005 |
| WO | WO 2007/085042 A1 | 8/2007 |
| WO | WO 2007/133777 A1 | 11/2007 |
| WO | WO 2007/133781 A2 | 11/2007 |

OTHER PUBLICATIONS

Mao et al., Formation and Characterization of Anchored POlymer Coatings on Alumina, 1998, Chemical Materials, vol. 10, pp. 509-517.*
European Search Report from EP Application No. 08 76 9362 mailed Nov. 2, 2010.
International Search Report for PCT/US08/063147 date of completion is Jul. 29, 2008 (2 pages).

\* cited by examiner

*Primary Examiner* — Dah-Wei Yuan
*Assistant Examiner* — Andrew Bowman

(57) ABSTRACT

An antimicrobial material is provided for use in forming textiles, medical devices, packaging materials, and the like, or coatings thereon. In some embodiments, the antimicrobial material may be utilized for bulk modification of an article. The antimicrobial material includes a furanone possessing vinyl and/or acrylate functional groups, optionally in combination with another monomer possessing vinyl and/or acrylate groups.

19 Claims, No Drawings

ANTIMICROBIAL MATERIALS AND COATINGS

CROSS-REFERENCE TO RELATED APPLICATIONS

This application is a National Stage Application of PCT/US2008/063147 under 35USC §371 (a), which claims priority of U.S. Provisional Patent Application Ser. No. 60/930,087 filed May 14, 2007, the disclosures of each of the above-identified applications are hereby incorporated by reference in their entirety.

TECHNICAL FIELD

The present disclosure relates to antimicrobial materials and coatings that may be used with textiles, medical devices, packaging materials, and the like.

BACKGROUND OF RELATED ART

The use of antimicrobial agents on medical devices such as sutures and/or packages containing said sutures has been previously disclosed. However, some medical devices may not provide effective levels of antimicrobial activity for a sufficient period of time. Moreover, antimicrobial agents on medical devices can be undesirably transferred to their packages, requiring the use of higher levels of antimicrobial agents in order to obtain the desired antimicrobial effect upon implantation of the suture or other medical device in vivo.

Accordingly, there is a need for medical devices, packaging materials and textiles that can retain enhanced antimicrobial efficacy.

SUMMARY

The present disclosure provides compositions including vinyl and/or acrylate functional furanones. These furanones may be utilized to form homopolymers or, in embodiments, may be combined with other monomers to form copolymers. These compositions may be suitable for forming articles such as textiles, medical devices, packaging materials, and the like, as well as coatings for such items.

In embodiments, the present disclosure provides methods which include providing an article; contacting the article with a first monomer possessing at least one vinyl or acrylate group in combination with a second monomer of formula:

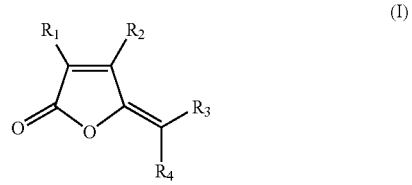

wherein $R_2$, $R_3$ and $R_4$ are independently or all H or halogen,
$R_1$ is a moiety such as H, halogen, formyl, carboxyl, cyano, ester, amide, alkyl, alkoxy, oxoalkyl, alkenyl, alkynyl, aryl and/or arylalkyl,
at least one of $R_1$, $R_2$, $R_3$ and $R_4$ are substituted with a moiety such as vinyl moieties and/or acrylate moieties; and
polymerizing the first monomer and the second monomer.

In other embodiments, the present disclosure provides methods which include contacting an article with a solution including a first monomer including at least one phosphorylcholine possessing at least one vinyl group of the formula:

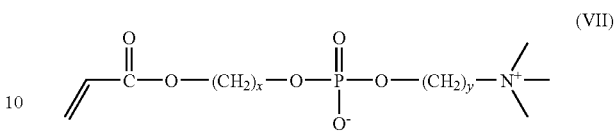

wherein x is from about 1 to about 10 and y is from about 1 to about 10, and a second monomer of formula:

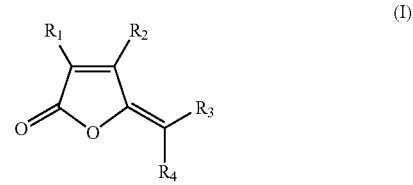

wherein $R_2$, $R_3$ and $R_4$ are independently or all H or halogen; and
$R_1$ is a moiety such as H, halogen, formyl, carboxyl, cyano, ester, amide, alkyl, alkoxy, oxoalkyl, alkenyl, alkynyl, aryl and/or arylalkyl,
wherein at least one of $R_1$, $R_2$, $R_3$ and $R_4$ are substituted with a moiety such as vinyl moieties and/or acrylate moieties; and
polymerizing the first monomer and the second monomer.

Compositions of the present disclosure may provide an easy and inexpensive method of incorporating or applying antimicrobial agents to a medical device, packaging material or textile that provides protection against microorganisms for extended periods of time, with minimal loss of the antimicrobial agents from the article surface and/or minimal transference of the antimicrobial agent to packaging materials, and the like. In this way, lower amounts of antimicrobial agents may be utilized to achieve the desired antimicrobial effect.

DETAILED DESCRIPTION

The present disclosure provides compositions suitable for textiles, medical devices, packaging materials, and the like, as well as coatings for such items. The compositions include vinyl and/or acrylate functional furanones. In embodiments, these furanones may be utilized to form homopolymers or, in embodiments, may be combined with other monomers to form copolymers. Copolymers herein may be bioabsorbable or nonabsorbable and include, but are not limited to, random, block, graft and/or segmented copolymers.

In embodiments, the furanones possessing vinyl and/or acrylate functional groups may also be halogenated. Halogenated furanones are known as inhibitors of quorum sensing. Quorum sensing, also known as bacterial signaling, is recognized as a general mechanism for gene regulation in many bacteria, and it allows bacteria to perform in unison such activities as bioluminescence, swarming, biofilm formation, production of proteolytic enzymes, synthesis of antibiotics, development of genetic competence, plasmid conjugal transfer, and spoliation. Quorum sensing is a universal regulatory mechanism used by both Gram-positive bacteria such as *Staphylococcus aureus*, *Streptococcus pneumoniae*, *Salmonella* enteritidis, Staphylococcus epidermidis, Bacillus subtilis, and the like, and Gram-negative bacteria such as Pseudomonas aeruginosa, Escherichia coli, Aeromonas hydrophila, and the like.

Thus, a quorum sensing inhibitor, such as the furanones described herein, may act as an antimicrobial agent by inhibiting microbial development and proliferation. In embodiments, a quorum sensing inhibitor may inhibit swarming motility and biofilm formation, both of which frequently underlie the pathophysiology of infectious diseases. The inhibition of swarming and biofilm formation may thus reduce bacterial burden and hence prevent infection and disease progression.

Halogenated furanones may also block quorum sensing and inhibit the growth of bacteria at amounts that are non-toxic to mammalian cells. Given their mechanism of action, halogenated furanones' antipathogenic properties may be effective against a broad spectrum of infectious agents and may be able to reduce and/or prevent colonization of both gram positive and gram negative bacteria, including those noted above.

In addition, unlike antibiotics and antiseptic compounds which kill microbes and carry the risk of inducing antimicrobial resistance, halogenated furanones do not exert such evolutionary pressures. Thus, antimicrobial resistance to an article coated with a composition of the present disclosure including a halogenated furanone is not a concern.

Suitable furanones possessing vinyl and/or acrylate groups for use in forming the copolymers in accordance with the present disclosure include, for example, compounds of the following formula:

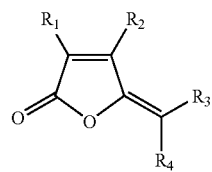

(I)

wherein $R_2$, $R_3$ and $R_4$ are independently or all H or halogen; and $R_1$ may be a moiety such as H, halogen, formyl, carboxyl, cyano, ester, amide, alkyl, alkoxy, oxoalkyl, alkenyl, alkynyl, aryl or arylalkyl, which moiety may optionally be substituted with one or more substituents; and/or interrupted by one or more hetero atoms; and/or straight chain, branched chain, hydrophobic, hydrophilic or fluorophilic, provided that at least one of $R_1$, $R_2$, $R_3$ and $R_4$ are substituted with a vinyl and/or acrylate group. In embodiments the furanone possessing a vinyl and/or acrylate group may also possess a halogen group.

As used herein, a substituted furanone or substituted moiety includes one possessing a group such as alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenylacyl, alkynylacyl, acylamino, diacylamino, acyloxy, alkylsulfonyloxy, heterocyclyl, heterocycloxy, heterocyclamino, haloheterocyclyl, alkylsulfenyl, carboalkoxy, alkylthio, acylthio, phosphorus-containing groups such as phosphono and phosphinyl, and combinations thereof.

As used herein, "alkyl", used either alone or in compound words such as "haloalkyl" or "alkylthio", includes straight chain or branched $C_{1-6}$ alkyl groups. Examples include methyl, ethyl, propyl, isopropyl and the like.

As used herein, "alkoxy" includes straight chain or branched alkoxy, in embodiments $C_{1-10}$ alkoxy such as methoxy, ethoxy, n-propoxy, isopropoxy and butoxy isomers.

As used herein, "alkenyl" includes groups formed from straight chain, branched or mono- or polycyclic alkenes including ethylenically mono- or poly-unsaturated alkyl or cycloalkyl groups as previously defined, in embodiments $C_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, and/or 1,3,5,7-cyclooctatetraenyl.

As used herein, "halogen" and/or "halogenated" includes fluorine, chlorine, bromine and/or iodine. In embodiments, a suitable halogen includes bromine.

As used herein, "heteroatoms" include O, N and/or S.

As used herein, "acyl" used either alone or in compound words such as "acyloxy", "acylthio", "acylamino" or diacylamino" includes carbamoyl, aliphatic acyl groups and acyl groups containing a heterocyclic ring which may be referred to as heterocyclic acyl, in embodiments $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopropylcarbonyl cyclobutylcarbonyl, cyclopentylcarbonyl or cyclohexylcarbonyl; alkylsulfonyl, such as methylsulfonyl or ethylsulfonyl; alkoxysulfonyl, such as methoxysulfonyl or ethoxysulfonyl; heterocyclylcarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; and/or heterocyclylglyoxyloyl, such as thiazolidinylglyoxyloyl or pyrrolidinylglyoxyloyl.

As used herein, "fluorophilic" includes the highly attractive interactions certain groups, such as highly fluorinated alkyl groups of $C_4$-$C_{10}$ chain length, have for perfluoroalkanes and perfluoroalkane polymers.

In other embodiments, a suitable furanone may be of the following formula:

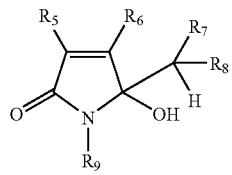

(II)

wherein $R_5$ and $R_6$ are independently H, halogen, hydroxy, substituted or unsubstituted alkyl, substituted or unsubstituted alkoxy, substituted or unsubstituted oxoalkyl, substituted or unsubstituted alkenyl, substituted or unsubstituted aryl, or substituted or unsubstituted arylalkyl, optionally interrupted by one or more hetero atoms, straight chain or branched chain, hydrophilic or fluorophilic, R_7 and R_8 are independently H, halogen, substituted or unsubstituted alkyl, substituted or unsubstituted alkoxy, substituted or unsubstituted aryl, or substituted or unsubstituted arylalkyl, and R_9 is H, hydroxy, substituted or unsubstituted alkyl, substituted or unsubstituted alkoxy, substituted or unsubstituted oxoalkyl, substituted or unsubstituted alkenyl, substituted or unsubstituted aryl or substituted or unsubstituted arylalkyl, optionally interrupted by one or more hetero atoms, straight chain or branched chain, hydrophilic or fluorophilic.

Specific examples of such compounds of formula II include, for example, the following:

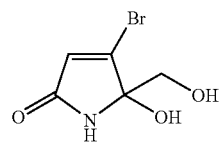
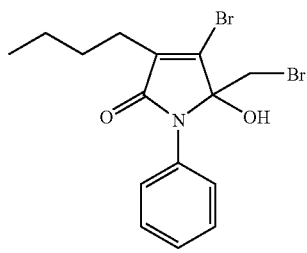
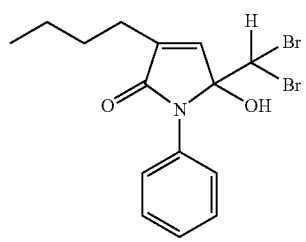
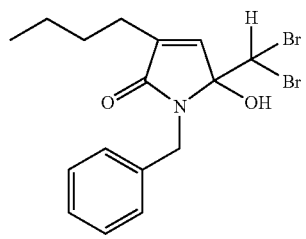
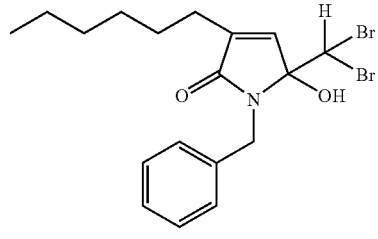
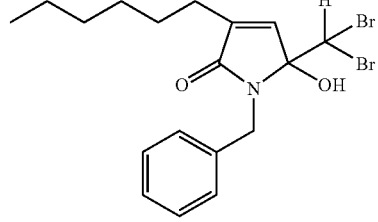
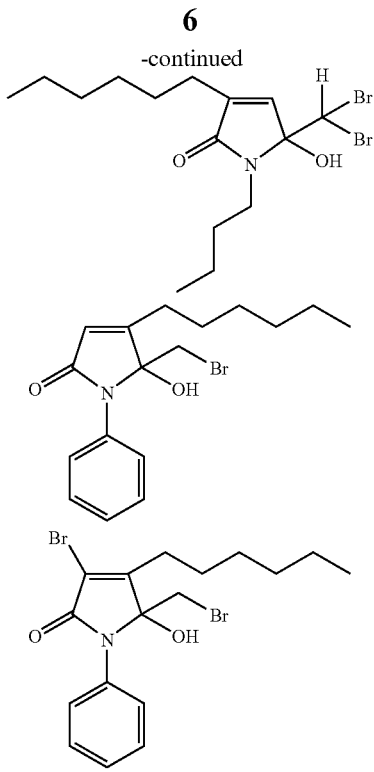

In some embodiments, the above furanones of formula II may be dehydrated to form another suitable furanone compound of the following formula III:

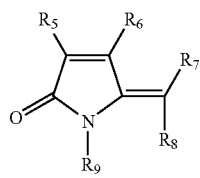

(III)

wherein $R_5$, $R_6$, $R_7$, $R_8$, and $R_9$ are as defined above.

Specific examples of compounds of formula III include the following:

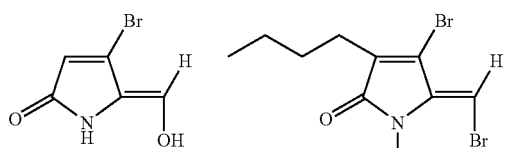
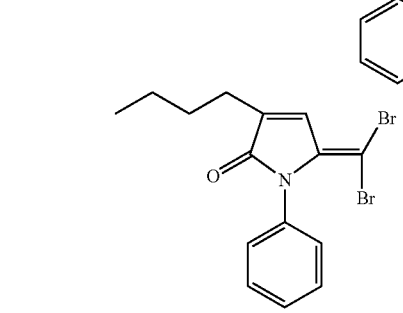

Specific examples of furanones of formula IV include, but are not limited to, the following:

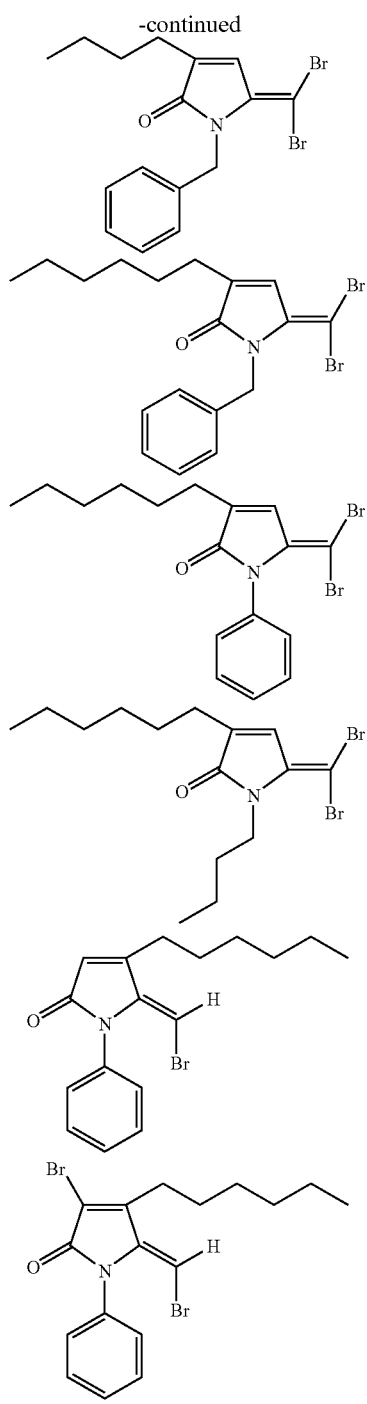
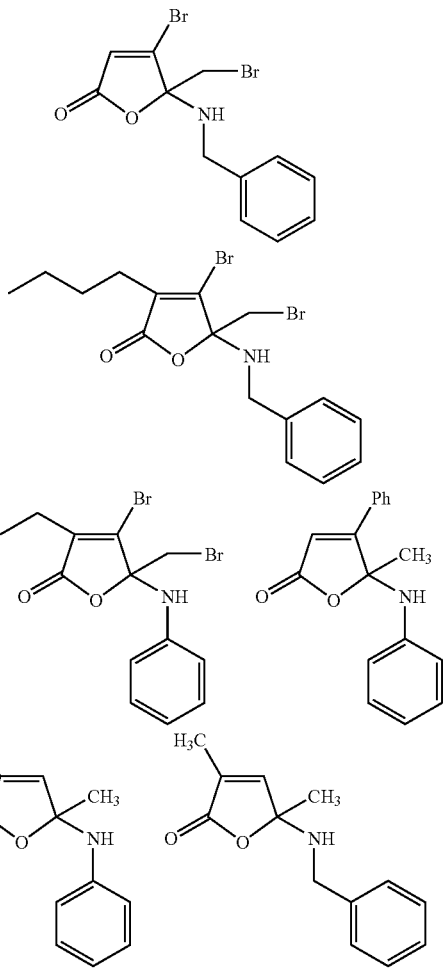

Other suitable furanone derivatives may include, in embodiments, those of the following formula:

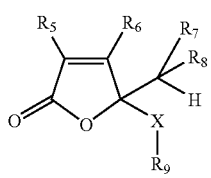

(IV)

wherein $R_5$, $R_6$, $R_7$, $R_8$ and $R_9$ are as defined above and X is O or $NR_5$.

Yet other suitable furanones include those of the following formula:

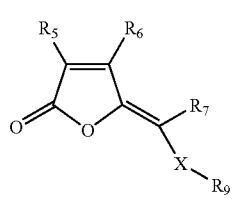

(V)

wherein $R_5$, $R_6$, $R_7$ and $R_9$ are as defined above, and X is O or $NR_5$.

Specific examples of furanones of formula V include, but are not limited to, the following:

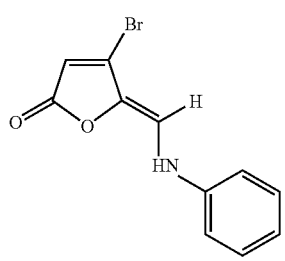

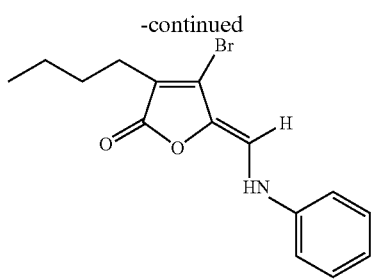
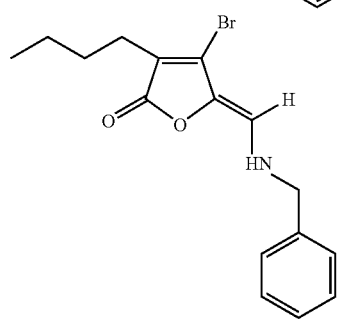
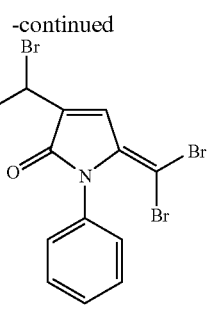
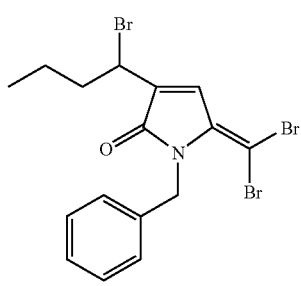
Yet other suitable furanones include those of the following formula:
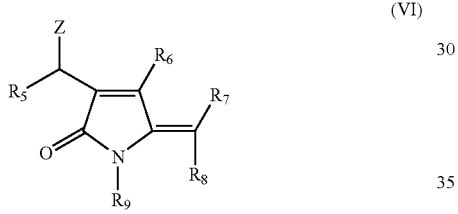
(VI)
wherein $R_5$, $R_6$, $R_7$, $R_8$ and $R_9$ are as defined above, and Z is $R_6$, halogen, $OC(O)R_6$, =O, amine, azide, thiol, mercaptoaryl, arylalkoxy, mercaptoarylalkyl, $SC(O)R_6$, $OS(O)_2R_6$, $NHC(O)R_6$, =$NR_6$, or $NHR_6$.
Specific examples of furanones of formula VI include, but are not limited to, the following:
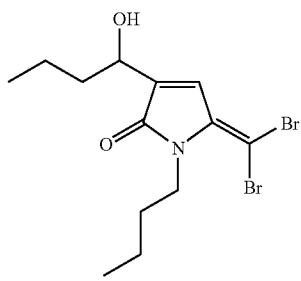
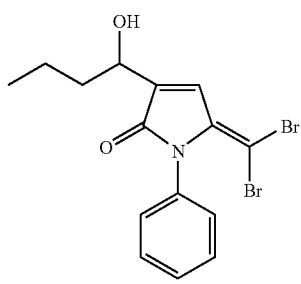
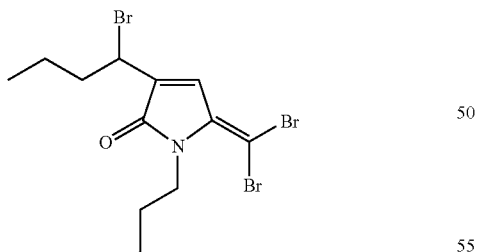
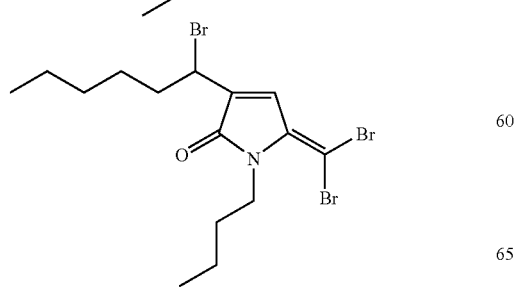
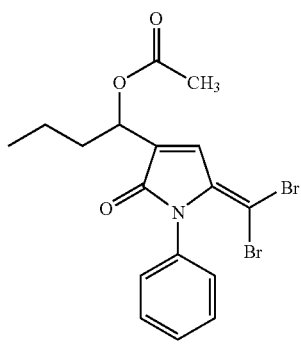

-continued

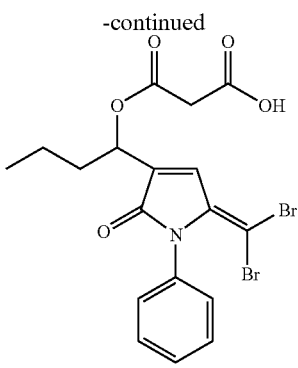

In embodiments, combinations of the foregoing furanones may be utilized.

As noted above, the furanones of the present disclosure may be utilized to form homopolymers or may be combined with other monomers to form copolymers. Suitable monomers which may be combined with the above furanones include, but are not limited to, other monomers possessing vinyl and/or acrylate groups. Such monomers may include drugs, peptides, proteins, polysaccharides, nucleic acids, lectins, lipids, and the like, possessing vinyl and/or acrylate groups.

Such monomers also include, for example, vinyl functional quaternary amines, acrylates including sodium acrylate, bisacrylate, butyl acrylate, sulfopropyl acrylate, hydroxy acrylates, polyethylene glycol acrylates, polyethylene glycol/polypropylene glycol acrylates, silicone acrylates, methacrylates including hydroxy ethyl methacrylate (HEMA) and sulfopropyl methacrylate, amides including acrylamide and diacrylamide, acids including acrylic acid, methacrylic acid and styrene sulfonic acid, vinyl pyrrolidones such as n-vinyl pyrrolidone, and phosphorylcholines such as 2-methacryloyloxyethyl phosphorylcholine (MPC), 2-acryloyloxyethyl phosphorylcholine, and the like, and combinations thereof. Other phosphorylcholines may be utilized, including phosphorylcholines based upon, or derived from, monomers including, but not limited to, 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butylphosphate, and combinations thereof. As used herein, "(meth)acryl" includes both methacryl and/or acryl groups.

In embodiments, suitable phosphorylcholines include those commercially available as PC 1059, PC 1036, PC 1062, PC 2028, PC 1071, PC 1015 and/or PC 2083 from Biocompatibles Limited (Middlesex, UK).

In other embodiments, suitable vinyl phosphorylcholines which may be combined with the furanones possessing vinyl and/or acrylate groups include those of the following formula:

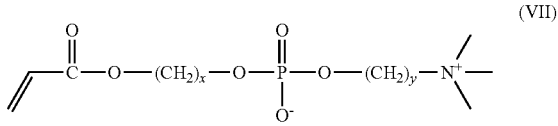

(VII)

wherein x is from about 1 to about 10, in embodiments from about 2 to about 6, and y is from about 1 to about 10, in embodiments from about 2 to about 6.

The copolymers of the present disclosure may be formed by polymerizing the above furanone possessing vinyl and/or acrylate groups with a phospholipid possessing at least one vinyl group.

Methods for forming polymers and/or copolymers with the above furanone monomers and co-monomers possessing vinyl or acrylate groups are within the purview of those skilled in the art. For example, a vinyl or acrylate furanone monomer may be dissolved in a co-monomer having vinyl or acrylate groups that is in a liquid state. For example, the furanone monomers and monomers having vinyl or acrylate groups can be mixed in a reaction vessel, optionally in combination with a suitable polymerization catalyst, if desired, and heated at temperatures from about 0° C. to about 250° C., in embodiments from about 25° C. to about 80° C., for a period of time from about 15 minutes to about 72 hours, in embodiments from about 60 minutes to about 24 hours.

In other embodiments, aqueous solutions or suspensions may be prepared possessing a furanone monomer, a co-monomer having vinyl and/or acrylate groups, or both. Suitable solvents which may be utilized in forming the solution include, for example, acetonitrile, acetic acid, dimethyl formamide, chloroform, dichloromethane, ethyl acetate, dimethyl sulfoxide, dioxane, benzene, toluene, methylene chloride, tetrahydrofuran, or where the polymer does not contain groups which react with protic solvents, water or an alkanol containing from about 1 to about 4 carbon atoms, e.g. methanol, ethanol or propan-2-ol. Alternatively, a mixture of any of the above solvents may be used.

In some embodiments the monomers may be combined in a single solvent. In other embodiments the furanone monomer may be placed in a first solvent, the co-monomer having vinyl and/or acrylate groups may be placed in a second solvent, and the two solutions then combined into a single solution or suspension, depending on the compatibility of the monomers and solvents.

Preparing a solution may be a relatively simple procedure and can be accomplished by blending, mixing, and the like. Solution polymerization conditions are within the purview of those skilled in the art and may include, for example, heating at temperatures from about 25° C. to about 120° C., in embodiments from about 40° C. to about 80° C., for a period of time from about 15 minutes to about 72 hours, in embodiments from about 60 minutes to about 24 hours. In embodiments where the two solutions containing the monomers are incompatible, a suspension or emulsion may be formed.

Where the solution is utilized to apply the furanone monomer, the co-monomer having vinyl and/or acrylate groups, or both, as a coating of a device, any solvent or combination of solvents should (1) be miscible with the coating components, and (2) not appreciably affect the integrity of any material used to form the article being coated, such as a suture.

Other methods for initiating polymerization are within the purview of those skilled in the art. For example, in some embodiments, a medical device may be swollen with a solution containing a furanone vinyl monomer, optionally in combination with a monomer having vinyl or acrylate groups, and polymerization initiated using high energy radiation such as gamma or e-beam, ultraviolet light, photoinitiators, chemical initiators, pulsed laser ablation deposition (PLAD), plasma energy, positron, and the like.

In embodiments, high energy radiation may be utilized to initiate polymerization. Where the device being coated is sensitive to high energy radiation, for example devices made of lactones, polypropylene, and the like, low doses may be applied to initiate polymerization. For example, in some embodiments gamma radiation may be applied in low doses of from about 0.05 Mrad to about 0.5 Mrad, in embodiments from about 0.1 Mrad to about 0.3 Mrad, to initiate polymerization.

Other methods for initiating polymerization are within the purview of those skilled in the art and include, for example, those disclosed in U.S. Pat. Nos. 5,290,548, 5,376,400, 5,804, 263, 5,885,566, and 6,387,379, the entire disclosures of each of which are incorporated by reference herein.

In other embodiments, a coating may be formed by placing an article in a degassed monomer solution possessing a furanone of the present disclosure optionally in combination with a co-monomer as described above. The solution may be at a temperature of from about 4° C. to about 50° C., in embodiments from about 10° C. to about 40° C. The device may be kept in the solution for a suitable period of time, in embodiments from about 1 hour to about 24 hours, in other embodiments from about 4 hours to about 20 hours. Following this incubation in solution, the device may be exposed to high energy radiation such as gamma or e-beam as described above. In other embodiments the device may be transferred to a fresh monomer solution and irradiated to commence polymerization in situ. Following polymerization, the modified device possessing a coating of the present disclosure may be washed to remove residual free polymer or monomer, or retained in the polymerization medium until it is ready for use. Where the radiation utilized to initiate polymerization is a dose of greater than about 2.5 Mrad, the application of radiation may act as a simultaneous polymerization initiator and a sterilization step.

The polymerization may be carried out in the presence of one or more polymerization initiators, such as benzoyl peroxide, 2,2'-azo-bis (2-methylpropionitrile), and/or benzoin methyl ether. Other polymerization initiators which may be used are within the purview of those skilled in the art and include, for example, those disclosed in "Polymer Handbook", 3rd edition, Ed. J. Brandrup and E. H. Immergut, Pub. Wiley-Interscience, New York, 1989.

Following polymerization, the polymer or article possessing the polymer coating may be removed from the polymerization medium and washed to remove any excess free polymer or residual monomer(s). The polymer or article having a grafted and interpenetrating coating of the polymer or copolymer may then be sterilized. In some cases, sterilization may occur by exposure to high energy radiation, such as gamma radiation. Thus, in some embodiments, radiation may be utilized to simultaneously initiate polymerization as well as sterilize an article possessing a coating of the present disclosure.

Some examples of furanone copolymers of the present disclosure include a furanone possessing vinyl and acrylate groups in combination with hydroxyethyl methacrylate (HEMA). The two monomers may be combined at a weight ratio of about 5:95 to about 30:70 furanone:HEMA and polymerized using gamma radiation to produce a poly(HEMA)-furanone copolymer or copolymer hydrogel. Such a composition may be useful with contact lenses, intraocular lenses, and similar devices that may be susceptible to infection that is difficult to treat. In addition, such devices may be incubated in a furanone monomer solution (utilizing a solvent that is a poor solvent for the device) to swell the device surface with monomer. The materials may then be exposed to low dose gamma radiation to initiate formation of the polymer and the formation of a graft/interpenetrating network coating. This could be utilized, in embodiments, in coating vascular grafts, meshes, intraocular lenses as described above, valves, sutures, stents, catheters, tissue engineered devices, tissue scaffolds, blood contact devices, shunts, endotracheal tubes, respiratory devices, anti-adhesion devices, sealants, adhesives, and the like.

Similarly, vinyl furanone monomers may be polymerized with vinyl pyrrolidones or vinyl phosphorylcholines including MPC to prepare hydrophilic copolymers suitable for coating articles of the present disclosure. Such coatings may improve biocompatibility and wettability, as well as provide a surface which makes it both biochemically difficult (due to the furanone) and sterically difficult (due to PVP or the phosphorylcholine) for bacteria to swarm and/or adhere to the surface of the device. Such coatings may be desirable for devices such as vascular grafts, meshes, catheters, contact lenses, sutures, stents, stent-grafts, and the like, where non-specific absorption of blood components, bacteria and the like may be difficult or problematic. Furanone-MPC copolymers and/or furanone-PVP copolymers may also be used to modify devices by exposure to gamma radiation.

In addition to forming homopolymers or copolymers, the above polymerization schemes may be utilized, in embodiments, to form coatings including the polymers formed from the furanones described herein. For example, in embodiments a medical device may be placed in a solution containing the furanone monomers and optionally the co-monomers described above, and polymerization allowed to occur whereby a graft or interpenetrating network of the furanone polymer or co-polymer is formed on the surface of the device. Solutions may also be used with conventional chemical couplers, for example silane based couplers, to covalently tether furanone vinyl polymers or copolymers described above to the surface of a medical device.

Suitable medical devices which may be formed of, or coated with, the furanone homopolymers or co-polymers described above include, but are not limited to, clips and other fasteners, staples, sutures, pins, screws, prosthetic devices, wound dressings, bandages, drug delivery devices, anastomosis rings, surgical blades, contact lenses, intraocular lenses, surgical meshes, stents, stent coatings, grafts, catheters, stent/grafts, knotless wound closures, sealants, adhesives, tissue scaffolds, stapling devices, buttresses, lapbands, orthopedic hardware, pacers, pacemakers, and other implantable devices. Fibers can be made from the furanone copolymers of the present disclosure. In embodiments, fibers made of furanone copolymers of the present disclosure may be knitted or woven with other fibers, either absorbable or nonabsorbable fibers, to form textiles. The fibers also can be made into non-woven materials to form fabrics, such as meshes and felts. Sutures may be monofilament or multifilament, including braided sutures. In other embodiments, sealants and/or adhesives may also be combined with the compositions of the present disclosure.

Medical devices can be formed from any material that has suitable physical properties for the intended use of the medical device including, in embodiments, the polymers and copolymers of the present disclosure. Medical devices can thus be formed of absorbable materials, nonabsorbable materials, and combinations thereof. Suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof. Suitable non-absorbable materials which may be utilized to form the medical device include polyolefins, such as polyethylene, polypropylene, copolymers of polyethylene and polypropylene, and blends of polyethylene and polypropylene.

In embodiments, a medical device treated in accordance with the present disclosure may be a suture. Sutures in accordance with the present disclosure may be monofilament or multifilament and may be made of any conventional material, including both bioabsorbable and non-bioabsorbable materials, such as surgical gut, silk, cotton, polyolefins such as polypropylene, polyamides, polyglycolic acids, polyesters such as polyethylene terephthalate and glycolide-lactide copolymers, and the like.

In embodiments, the suture may be made of a polyolefin. Suitable polyolefins include polyethylene, polypropylene, copolymers of polyethylene and polypropylene, and blends of polyethylene and polypropylene. In some embodiments, polypropylene can be utilized to form the suture. The polypropylene can be isotactic polypropylene or a mixture of isotactic and syndiotactic or atactic polypropylene.

In other embodiments, the suture may be made from synthetic absorbable polymers such as those made from glycolide, lactide, caprolactone, alkylene carbonates (i.e., trimethylene carbonate, tetramethylene carbonate, etc.), dioxanones, and copolymers and combinations thereof. One combination which may be utilized includes glycolide and lactide based polyesters, including copolymers of glycolide and lactide.

As noted above, the suture can be monofilament or multifilament. Where the suture is a monofilament, methods for producing such sutures are within the purview of those skilled in the art. Such methods include forming a suture material, such as a polyolefin resin, and extruding, drawing and annealing the resin to form the monofilament.

Where the sutures are made of multiple filaments, the suture can be made using any technique within the purview of one skilled in the art such as, for example, braiding, weaving or knitting. The filaments may also be combined to produce a non-woven suture. The filaments themselves may be drawn, oriented, crinkled, twisted, commingled or air entangled to form yarns as part of the suture forming process.

In embodiments a multifilament suture of the present disclosure can be produced by braiding. The braiding can be done by any method within the purview of those skilled in the art. For example, braid constructions for sutures and other medical devices are described in U.S. Pat. Nos. 5,019,093, 5,059,213, 5,133,738, 5,181,923, 5,226,912, 5,261,886, 5,306,289, 5,318,575, 5,370,031, 5,383,387, 5,662,682, 5,667,528, and 6,203,564, the entire disclosures of each of which are incorporated by reference herein.

Once the suture is constructed, it can be sterilized by any means within the purview of those skilled in the art.

In some cases a tubular braid, or sheath, can be constructed about a core structure which is fed through the center of a braider. Known tubular braided sutures, including those possessing cores, are disclosed, e.g., in U.S. Pat. Nos. 3,187,752, 3,565,077, 4,014,973, 4,043,344, and 4,047,533.

Any suitable amount of furanone may be utilized in forming a device or a coating of the present disclosure. As noted above, due to their excellent antibacterial activity, furanones may be utilized in low level dosages which are capable of imparting anti-microbial properties to the article to which the coating is applied. In embodiments, the amount of furanone present in a coating of the present disclosure may be from about 5 parts per million (ppm) to about 1000 ppm, in embodiments from about 20 ppm to about 800 ppm, in other embodiments from about 100 ppm to about 600 ppm. The exact amount of the furanone in the device and/or antimicrobial coating will depend upon a number of factors, such as the particular furanone used, the composition of the article being contacted, and the choice of polymer utilized in the coating material.

In some embodiments, compositions of the present disclosure may also contain a fatty acid component such as a fatty acid, a fatty acid salt, or a salt of a fatty acid ester. Suitable fatty acids may be saturated or unsaturated, and include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, in embodiments those having from about 12 to about 22 carbon atoms, and mixtures thereof. Fatty acid salts including the calcium, magnesium, barium, aluminum, and zinc salts of stearic, palmitic and oleic acids may be useful in some embodiments of the present disclosure. Some useful salts include commercial "food grade" calcium stearate which contains a mixture of about one-third $C_{16}$ and two-thirds $C_{18}$ fatty acids, with small amounts of the $C_{14}$ and $C_{22}$ fatty acids.

Suitable salts of fatty acid esters which may be included in the compositions and/or coatings of the present disclosure include calcium, magnesium, aluminum, barium, or zinc stearoyl lactylate; calcium, magnesium, aluminum, barium, or zinc palmityl lactylate; and/or calcium, magnesium, aluminum, barium, or zinc olelyl lactylate. In embodiments; calcium stearoyl-2-lactylate (such as the calcium stearoyl-2-lactylate commercially available under the tradename VERV from American Ingredients Co., Kansas City, Mo.) may be utilized. Other fatty acid ester salts which may be utilized include lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate.

Where utilized, the amount of fatty acid component can be from about 5 percent to about 60 percent by weight of the total composition. In embodiments, the fatty acid component may be present in an amount from about 15 percent to about 55 percent by weight of the total composition.

In other embodiments, the above furanones and optional co-monomers may also be combined with an additional polymer to form a device and/or coating. Any polymer suitable for use as a device and/or coating may be utilized in accordance with the present disclosure. Polymers may be bioabsorbable or nonabsorbable. In embodiments, a bioabsorbable film-forming polymer may be utilized in a device and/or coating of the present disclosure. Film-forming polymers which may be utilized in the device and/or coating are within the purview of those skilled in the art and include those containing linkages derived from monomers including, for example, glycolide, lactide, glycolic acid, lactic acid, caprolactone, trimethylene carbonate, dioxanones, dioxepanones, and the like, and homopolymers, copolymers and combinations thereof.

In embodiments, the film-forming polymer may include a caprolactone containing copolymer as described in U.S. Pat. No. 5,716,376, the entire disclosure of which is incorporated by reference herein. Such a caprolactone containing copolymer can be obtained by polymerizing a major amount of epsilon-caprolactone and a minor amount of at least one other copolymerizable monomer or mixture of such monomers in the presence of a hydroxyl-functional initiator, such as a polyhydric alcohol initiator.

Monomers which can be copolymerized with epsilon-caprolactone include alkylene carbonates such as trimethylene carbonate, tetramethylene carbonate, dimethyl trimethylene carbonate; dioxanones; dioxepanones; absorbable cyclic amides; absorbable cyclic ether-esters derived from crown ethers; hydroxyacids capable of esterification, including alpha hydroxy acids (such as glycolic acid and lactic acid) and beta hydroxyacids (such as beta hydroxybutyric acid and gamma hydroxyvaleric acid); polyalkyl ethers (such as polyethylene glycol), and combinations thereof. In embodiments, glycolide can be utilized as the comonomer with epsilon-caprolactone in the film-forming polymer.

Suitable polyhydric alcohol initiators which may be utilized in preparing the film-forming polymer include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being utilized in some embodiments.

The polyhydric alcohol initiator can be employed in small amounts, in embodiments from about 0.01 to about 5 weight percent of the total monomer mixture, in other embodiments from about 0.1 to about 3 weight percent of the total monomer mixture.

Where utilized, the film-forming copolymer can contain from about 70 to about 98 weight percent epsilon-caprolactone derived units, in embodiments from about 80 to about 95 weight percent epsilon-caprolactone derived units, the balance of the copolymer being derived from the other copolymerizable monomer(s), such as glycolide.

In embodiments a film-forming polymer, such as the caprolactone/glycolide copolymer described above, can be present in an amount from about 45 to about 60 weight percent of the composition of the present disclosure and the fatty acid component, such as a fatty acid salt or a salt of a fatty acid ester, can be present in an amount from about 40 to about 55 weight percent of the composition of the present disclosure. In embodiments, the film-forming polymer, such as the caprolactone/glycolide copolymer described above, can be present in an amount from about 50 to about 55 weight percent of the composition of the present disclosure and the fatty acid component can be present in an amount from about 45 to about 50 weight percent of the composition of the present disclosure.

Any known technique may be employed for applying a coating, for example as a solution or suspension, to an article. Suitable techniques include dipping, spraying, wiping and brushing. The article wetted with the coating solution or suspension may be subsequently passed through or held in a drying oven for a time and at a temperature sufficient to vaporize and drive off the solvent.

Articles made from, or coated with, a composition of the present disclosure may be formed from any material in need of improved resistance to bacteria. Such articles include, but are not limited to, textiles, packaging materials, medical devices, and the like.

Textiles which may be made from, or coated with, coatings of the present disclosure include those made of natural fibers, synthetic fibers, blends of natural fibers, blends of synthetic fibers, and blends of natural fibers with synthetic fibers. Suitable materials utilized to form textiles include polyesters, polyamides, polyolefins, halogenated polymers, polyester/polyethers, polyurethanes, homopolymers thereof, copolymers thereof, and combinations thereof. Specific examples of suitable materials include polyethylene, polypropylene, polybutylene, polyvinyl chloride, polyethylene terephthalate, nylon 6, and nylon 6,6.

Packaging materials which may be made from, or coated with, compositions of the present disclosure include packaging for products such as medical devices, pharmaceuticals, textiles, consumer goods, foods, and the like. Packaging materials may be formed of any suitable material within the purview of those skilled in the art.

Textiles, including individual fibers and fabrics made of multiple fibers, may be formed and/or coated in a similar manner.

A suture made from, or coated with, a composition of the present disclosure will possess antimicrobial properties. In embodiments, a suture of the present disclosure may possess an elongate structure and be formed from at least one polymeric filament, in embodiments, multiple filaments. The filaments may be formed from a polymeric material that is absorbable under physiological conditions, and a coating including the composition of the present disclosure may be placed thereon.

In embodiments, a suture in accordance with the present disclosure may be attached to any surgical needle within the purview of those skilled in the art to produce a needled suture. Such a needled suture is depicted in the FIGURE, with suture 101 attached to needle 100. Wounds may be sutured by passing a needled suture through tissue to create wound closure. The needle may then be removed from the suture and the suture tied. The suture may remain in the tissue and help prevent contamination and infection of said tissue by virtue of its antimicrobial properties, thereby promoting wound healing and minimizing infection. The suture coating also advantageously enhances the surgeon's ability to pass the suture through tissue, and increases the ease and security with which he/she can tie the suture.

Medical devices and packaging materials in accordance with this disclosure can be sterilized in accordance with techniques within the purview of those skilled in the art.

Coatings of the present disclosure, including halogenated furanones described herein, remain attached to the surface of the article during the processing, handling, and storage of the article. This minimizes the loss or transfer of the halogenated furanones from an article to any packaging, from any packaging to any article, the environment, etc.

If desired, the composition of the present disclosure can optionally contain additional components, e.g., dyes, antimicrobial agents, growth factors, anti-inflammatory agents, and the like. The term "antimicrobial agent" as used in the present disclosure includes antibiotics, antiseptics, disinfectants and combinations thereof. In embodiments, the antimicrobial agent may be an antiseptic, such as triclosan.

Classes of antibiotics that can be used in the composition include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam.

In other embodiments, silver salts, including silver salts of ionic furanones, may be added for their antimicrobial properties.

Examples of antiseptics and disinfectants which may be utilized in the compositions include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2' hydroxy-diphenylether); furan medical preparations like nitrofurantoin and nitrofurazone; methenamine; aldehydes like glutaraldehyde and formaldehyde; and alcohols. In some embodiments, at least one of the antimicrobial agents may be an antiseptic, such as triclosan.

The antimicrobial compositions of the present disclosure may contain various optional ingredients, such as stabilizing agents, thickeners, colors, and the like. The optional ingredients may be present in an amount of up to about 10% of the total weight of the antimicrobial composition.

As low amounts of furanones are required in compositions of the present disclosure, existing formulations and manufacturing processes need only minimal modifications to produce the compositions described herein. This ease of formulation and production may reduce both the time and cost necessary to prepare compositions of the present disclosure, compared with adding other antimicrobial agents to existing compositions.

While the above description contains many specifics, these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:
1. A method comprising:
providing an article;
contacting the article with a first monomer comprising at least one vinyl or acrylate group in combination with a second monomer of formula:

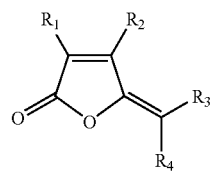

(I)

wherein $R_2$, $R_3$ and $R_4$ are independently or all H or halogen, $R_1$ is a moiety selected from the group consisting of H, halogen, formyl, carboxyl, cyano, ester, amide, alkyl, alkoxy, oxoalkyl, alkenyl, alkynyl, aryl and arylalkyl, at least one of $R_1$, $R_2$, $R_3$ and $R_4$ are substituted with a moiety selected from the group consisting of vinyl moieties and acrylate moieties; and polymerizing the first monomer and the second monomer wherein the first monomer is selected from the group consisting of 2-methacryloyloxyethyl phosphorylcholine, 2-acryloyloxyethyl phosphorylcholine, and combinations thereof.

2. The method of claim 1, wherein the first monomer and the second monomer are in a solution comprising at least one solvent selected from the group consisting of liquid vinyl monomers, water, organic solvents, and combinations thereof.

3. The method of claim 1, wherein the second monomer comprises a vinyl furanone.

4. The method of claim 1, wherein polymerizing the first monomer and the second monomer occurs in situ.

5. The method of claim 1, wherein polymerizing the first monomer and the second monomer occurs in the presence of an initiator selected from the group consisting of photoinitiators, chemical initiators, and combinations thereof.

6. The method of claim 1, wherein polymerizing the first monomer and the second monomer further comprises the application of at least one energy source selected from the group consisting of gamma radiation, e-beam radiation, ultraviolet light, pulsed laser ablation deposition, plasma energy, positron, and combinations thereof.

7. The method of claim 1, wherein polymerizing the first monomer and the second monomer forms a polymer on or within the article.

8. The method of claim 1, wherein the article is selected from the group consisting of sutures, surgical meshes, contact lenses, intraocular lenses, staples, clips, buttresses, lapbands, catheters, bandages, stents, grafts, stent/grafts, knotless wound closures, sealants, adhesives, tissue scaffolds, pins, screws, orthopedic hardware, pacers, and pacemakers.

9. A method comprising:
contacting an article with a solution comprising a first monomer comprising at least one phosphorylcholine possessing at least one vinyl group of the formula:

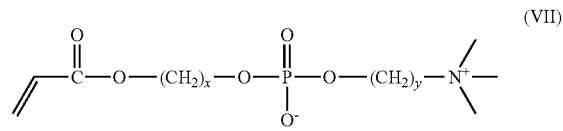

(VII)

wherein x is from about 1 to about 10 and y is from about 1 to about 10 and a second monomer of formula

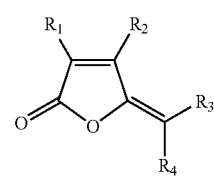

(I)

wherein $R_2$, $R_3$ and $R_4$ are independently or all H or halogen; and

R₁ is a moiety selected from the group consisting of H, halogen, formyl, carboxyl, cyano, ester, amide, alkyl, alkoxy, oxoalkyl, alkenyl, alkynyl, aryl and arylalkyl,
wherein at least one of R₁, R₂, R₃ and R₄ are substituted with a moiety selected from the group consisting of vinyl moieties and acrylate moieties; and
polymerizing the first monomer and the second monomer.

10. The method of claim 9, wherein the solution comprises at least one solvent selected from the group consisting of liquid vinyl monomers, water, organic solvents, and combinations thereof.

11. The method of claim 9, wherein the first monomer is selected from the group consisting of 2-methacryloyloxyethyl phosphorylcholine, 2-acryloyloxyethyl phosphorylcholine and combinations thereof.

12. The method of claim 9, wherein the second monomer comprises a vinyl furanone.

13. The method of claim 9, wherein the polymerization occurs in situ.

14. The method of claim 9, wherein the solution further comprises at least one additional monomer selected from the group consisting of vinyl monomers and acrylate monomers.

15. The method of claim 9, wherein the solution further comprises at least one additional monomer selected from the group consisting of vinyl functional quaternary amines, hydroxyethyl methacrylate, n-vinyl pyrrolidone, sodium acrylate, bis-acrylate, styrene sulfonic acid, butyl acrylate, sulfopropyl acrylate, sulfopropyl methacylate, acrylamide, diacrylamide, methacrylic acid, acrylic acid, polyethylene glycol acrylates, polyethylene glycol/polypropylene glycol acrylates, silicone acrylates, and combinations thereof.

16. The method of claim 9, wherein polymerizing the first monomer and the second monomer occurs in the presence of an initiator selected from the group consisting of photoinitiators, chemical initiators, and combinations thereof.

17. The method of claim 9, wherein polymerizing the first monomer and the second monomer further comprises the application of at least one energy source selected from the group consisting of gamma radiation, e-beam radiation, ultraviolet light, pulsed laser ablation deposition, plasma energy, positron, and combinations thereof.

18. The method of claim 9, wherein polymerizing the first monomer and the second monomer forms a polymer on or within the article.

19. The method of claim 9, wherein the article is selected from the group consisting of sutures, surgical meshes, contact lenses, intraocular lenses, staples, clips, buttresses, lapbands, catheters, bandages, stents, grafts, stent/grafts, knotless wound closures, sealants, adhesives, tissue scaffolds, pins, screws, orthopedic hardware, pacers, and pacemakers.

* * * * *